United States Patent
Windrix

(10) Patent No.: US 10,842,744 B1
(45) Date of Patent: Nov. 24, 2020

(54) PERFORMANCE PRODUCT

(71) Applicant: Jesse Windrix, Allen, TX (US)

(72) Inventor: Jesse Windrix, Allen, TX (US)

( * ) Notice: Subject to any disclaimer, the term of this patent is extended or adjusted under 35 U.S.C. 154(b) by 0 days.

(21) Appl. No.: 16/261,485

(22) Filed: Jan. 29, 2019

Related U.S. Application Data

(60) Provisional application No. 62/623,650, filed on Jan. 30, 2018.

(51) Int. Cl.

| | | |
|---|---|---|
| *A61K 9/107* | (2006.01) | |
| *A61K 31/047* | (2006.01) | |
| *A61K 9/00* | (2006.01) | |
| *A61K 33/00* | (2006.01) | |
| *A61K 31/522* | (2006.01) | |
| *A23L 33/10* | (2016.01) | |
| *A61K 31/198* | (2006.01) | |

(52) U.S. Cl.
CPC .............. *A61K 9/107* (2013.01); *A23L 33/10* (2016.08); *A61K 9/0095* (2013.01); *A61K 31/047* (2013.01); *A61K 31/198* (2013.01); *A61K 31/522* (2013.01); *A61K 33/00* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 6,399,661 B1 * | 6/2002 | Golini | ................. | A61K 9/0095 514/565 |
| 6,544,530 B1 * | 4/2003 | Friedman | ................. | A61K 8/06 424/400 |
| 2005/0142154 A1 * | 6/2005 | Blatt | ...................... | A61Q 19/00 424/401 |
| 2009/0130029 A1 * | 5/2009 | Tamarkin | ............... | A61K 8/046 424/47 |
| 2010/0092441 A1 * | 4/2010 | Lundberg | ............... | A61K 31/05 424/93.45 |
| 2014/0106008 A1 * | 4/2014 | Venter | .................... | A01N 31/02 424/682 |
| 2016/0101391 A1 * | 4/2016 | Wey | .......................... | C10L 1/32 366/177.1 |

OTHER PUBLICATIONS

AH Saberi, Y Fang, DJ McClements. "Effect of glycerol on formation, stability, and properties of vitamin-E enriched nanoemulsions produced using spontaneous emulsification." Journal of Colloid and Interface Science, vol. 411, 2013, pp. 105-113. (Year: 2013).*

S Wakisaka, T Nishmura, S Gohtani. "O/W Nan-Emulsion Formation Using an Isothermal Low-Energy Emulsification Method in a Mixture of Polyglycerol Polyricinoleate and Hexaglycerol Monolaurate with Glycerol System." Journal of Oleo Science, vol. 64 (4), 2015, pp. 405-413. (Year: 2015).*

* cited by examiner

*Primary Examiner* — Isaac Shomer

(74) *Attorney, Agent, or Firm* — Kirby Drake

(57) ABSTRACT

Glycerol may be placed into liquid form and consumed as a pre-workout or pump product to increase hydration during exercise. Liquid-based glycerol products may embrace the hygroscopic properties associated with glycerol by delivering glycerol in a liquid form that is more compatible and complementary to these physical properties. A liquid suspension of a glycerol-based product may overcome the hygroscopic disadvantages experienced with glycerol when provided in a powder form, chiefly poor mixing, instability during storage, shipping or packaging, as well as dosing limitations.

4 Claims, No Drawings

PERFORMANCE PRODUCT

CROSS-REFERENCE TO PRIOR APPLICATION

This application claims priority to U.S. Provisional Application No. 62/623,650 filed Jan. 30, 2018 and entitled "Performance Product," the disclosure of which is incorporated by reference in its entirety.

FIELD OF THE DISCLOSURE

The present disclosure generally relates to liquid performance products, and more specifically, liquid performance products in the form of glycerol pre-workout or pump products.

BACKGROUND

There are many nutritional supplement products that fall into the category of "pump" products. A muscle pump occurs when fluid fills up the muscle cells. Pump products are marketed to assist performance and appearance during exercise, and their use may be associated with a subjective feeling of tightness in the muscle group that is being exercised. This is a key characteristic of "pump" as referred to in the nutritional supplement industry and athletic community.

Glycerol (1,2,3-propanetriol) is the backbone of fats known as triglycerides, and glycerol is the part of triglycerides that is not stored as fat. Rather, the liver converts glycerol to glucose for use as fuel for the body. Glycerol has been used by runners and other endurance athletes because it is a hydrating agent with strong osmotic properties, thereby allowing athletes to increase their body fluid content and maintain it for longer to boost exercise performance. Glycerol has been marketed as a pump product, but it has only been used in powder form. This has several disadvantages. Glycerol is highly hygroscopic, which can result in handling and storage issues. As the concentration and time increases, there may be more powder clumping. Further, because of this physical property, most formulations are limited by total amount (up to 2 g/dose), resulting in sub-therapeutic dosing as compared to studied therapeutic doses.

SUMMARY

Embodiments of the present disclosure may provide a stable liquid formulation of glycerol for use as a nutritional supplement pre-workout or pump product. Liquid glycerol according to embodiments of the present disclosure may be provided in a ready-to-drink serving or as a pump shot.

Other embodiments of the present disclosure may provide a method for producing a liquid glycerol formulation, the method comprising: processing glycerol to micronize the glycerol in solution, thereby increasing homogeneity of the glycerol in solution; and combining the glycerol in solution with one or more emulsifying agents. The glycerol may be processed using a high shear pump or homogenizer. The one or more emulsifying agents may be selected from the group comprising: agar, albumin, alginates, casein, egg yolk, glycerol monostearate, gums, animal fat, vegetable oil, lecithin, soy lecithin, and sunflower lecithin. The one or more emulsifying agents may be selected based on one or more factors selected from the group comprising: size of a desired molecular structure, desired texture, and desired flavor. The method may further comprise adding one more flavorings to the glycerol in solution. The method also may further comprise adding one or more ingredients to perform performance. The one or more ingredients may be selected from the group comprising: sodium nitrate, creatine, caffeine, stem ingredients, amino acids, and hydration-related ingredients. The one or more ingredients may be sodium nitrate to improve performance as a pump shot. The one or more ingredients may be creatine and/or caffeine to improve performance as a pre-workout product. The method also may include adding the emulsion of glycerol to a pre-workout product or pump shot.

Further embodiments of the present disclosure may include a liquid glycerol formulation for use as a nutritional supplement pre-workout or pump product, the formulation comprising: micronized glycerol in solution; one or more emulsifying agents, the one or more emulsifying agents selected from the group comprising: agar, albumin, alginates, casein, egg yolk, glycerol monostearate, gums, animal fat, vegetable oil, lecithin, soy lecithin, and sunflower lecithin; and one or more ingredients to perform performance, the one or more ingredients selected from the group comprising: sodium nitrate, creatine, caffeine, stem ingredients, amino acids, and hydration-related ingredients.

Additional embodiments of the present disclosure may provide a liquid glycerol formulation for use as a nutritional supplement pre-workout or pump product, the formulation comprising: micronized glycerol in solution; and one or more emulsifying agents that encapsulate the glycerol to form an emulsion of glycerol, wherein the emulsion of glycerol may remain in liquid form, thereby retaining the hygroscopic properties of the glycerol and increasing hydration when delivered as the nutritional supplement pre-workout or pump product. The one or more emulsifying agents may be selected from the group comprising: agar, albumin, alginates, casein, egg yolk, glycerol monostearate, gums, animal fat, vegetable oil, lecithin, soy lecithin, and sunflower lecithin. The formulation may further comprise one more flavorings added to the glycerol in solution. The formulation also may comprise one or more ingredients to perform performance, the one or more ingredients selected from the group comprising: sodium nitrate, creatine, caffeine, stem ingredients, amino acids, and hydration-related ingredients. The one or more ingredients may be sodium nitrate to improve performance as a pump shot. The one or more ingredients may be creatine and/or caffeine to improve performance as a pre-workout product. The emulsion of glycerol may be added to a pre-workout product or pump shot.

Other technical features may be readily apparent to one skilled in the art from the following figures, descriptions and claims.

DETAILED DESCRIPTION

Embodiments of the present disclosure may provide a stable liquid formulation of glycerol for use as a nutritional supplement pre-workout or a "pump" product. It may be provided in a full ready-to-drink serving or as a pump shot that may be provided in a smaller single serving bottle or container.

Glycerol is a sugar alcohol that contains three hydroxyl groups. These three hydroxyl groups provide for extreme solubility. By consuming glycerol as a pre-workout or pump product, this may increase hydration during exercise. Liquid-based glycerol products according to embodiments of the present disclosure may embrace the hygroscopic properties associated with glycerol by delivering glycerol in a liquid form that is more compatible and complementary to these physical properties. More specifically, according to embodiments of the present disclosure, a liquid suspension of a glycerol-based product may overcome the hygroscopic disadvantages experienced with glycerol when provided in a powder form, chiefly poor mixing, instability during storage, shipping or packaging, as well as dosing limitations.

In embodiments of the present disclosure, a liquid glycerol formulation may be provided. Glycerol may be processed through a high shear pump or homogenizer to micronize the glycerol in solution and increase the homogeneity of the product in solution. By sending the glycerol through a high shear pump or homogenizer, this may encapsulate the glycerol by using an emulsifier such as soy or sunflower lecithin, thereby improving how the glycerol may be absorbed when ingested by a user. By suspending glycerol in an emulsion, the glycerol is not further diluted, and thus, the hydrophilic properties may remain strong. The emulsion of glycerol may then be added into another product if desired.

The glycerol once placed in solution may then be combined with one or more emulsifying agents to aid in mixing according to some embodiments of the present disclosure. Emulsifying agents may include, but are not limited to, agar, albumin, alginates, casein, egg yolk, glycerol monostearate, gums, animal fat, vegetable oil, lecithin, and combinations thereof. It should be appreciated that emulsifying agents may be selected depending on various factors including, but not limited to, the size of the molecular structure desired, the texture desired, and the flavor desired in the resultant product.

In embodiments of the present disclosure, one or more flavorings and/or other ingredients may be added to the glycerol in solution to form an efficacious and palatable serving of liquid glycerol. Other ingredients may include those that may improve performance as a pre-workout or pump product including, but not limited to, sodium nitrate, creatine and caffeine. It should be appreciated that sodium nitrate may be added to a pump shot, while creatine and caffeine may be added to a pre-workout product in embodiments of the present disclosure. In addition, stem ingredients, amino acids, or other hydration-related ingredients may be incorporated into formulations according to embodiments of the present disclosure.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A method for producing a liquid glycerol nutritional supplement pump shot for oral consumption, the method consisting of:
   processing glycerol with a high-shear pump or homogenizer;
   combining the glycerol with one or more emulsifying agents; and
   adding sodium nitrate and optionally one or more flavorings to the combination of the glycerol and the one or more emulsifying agents to form the nutritional supplement pump shot for oral consumption.

2. The method of claim 1, wherein the one or more emulsifying agents are selected from the group consisting of agar, albumin, alginates, casein, egg yolk, glycerol monostearate, gums, animal fat, vegetable oil, lecithin, soy lecithin, and sunflower lecithin.

3. A method for producing a liquid glycerol nutritional supplement pre-workout product for oral consumption, the method consisting of:
   processing glycerol with a high-shear pump or homogenizer;
   combining the glycerol with one or more emulsifying agents; and
   adding creatine and/or caffeine and optionally one or more flavorings to the combination of the glycerol in solution and the one or more emulsifying agents to form the nutritional supplement pre-workout product for oral consumption.

4. The method of claim 3, wherein the one or more emulsifying agents are selected from the group consisting of agar, albumin, alginates, casein, egg yolk, glycerol monostearate, gums, animal fat, vegetable oil, lecithin, soy lecithin, and sunflower lecithin.

* * * * *